(12) United States Patent
Cossar et al.

(10) Patent No.: US 10,017,710 B2
(45) Date of Patent: Jul. 10, 2018

(54) METHOD OF SEPARATING MANNOSYLERYTHRITOL LIPIDS

(71) Applicant: Croda International PLC, Goole Yorkshire (GB)

(72) Inventors: John Douglas Cossar, Guelph (CA); Raymond John Marriott, Northants (GB); Luis Martin Navarro, Saragossa (ES)

(73) Assignee: CRODA INTERNATIONAL PLC, Yorkshire (GB)

( * ) Notice: Subject to any disclaimer, the term of this patent is extended or adjusted under 35 U.S.C. 154(b) by 0 days.

(21) Appl. No.: 15/561,703

(22) PCT Filed: Feb. 9, 2016

(86) PCT No.: PCT/GB2016/050297
§ 371 (c)(1),
(2) Date: Sep. 26, 2017

(87) PCT Pub. No.: WO2016/156781
PCT Pub. Date: Oct. 6, 2016

(65) Prior Publication Data
US 2018/0094208 A1   Apr. 5, 2018

(30) Foreign Application Priority Data

Mar. 27, 2015 (GB) .................................. 1505287.1

(51) Int. Cl.
*C11B 3/00* (2006.01)
*C11B 1/10* (2006.01)
(Continued)

(52) U.S. Cl.
CPC .............. *C11B 1/104* (2013.01); *A23D 9/013* (2013.01); *B01D 11/0403* (2013.01);
(Continued)

(58) Field of Classification Search
CPC ....................................................... C11B 1/104
(Continued)

(56) References Cited

U.S. PATENT DOCUMENTS

| 5,417,879 | A  | 3/1995 | Hall et al. |
| 5,520,839 | A  | 5/1996 | Hall et al. |
| 2012/0220464 | A1 | 8/2012 | Giessler-Blank et al. |

FOREIGN PATENT DOCUMENTS

| EP | 1964546 A1 | 9/2008 |
| EP | 2578204 A1 | 4/2013 |

(Continued)

OTHER PUBLICATIONS

International Search Report and Written Opinion for International Application No. PCT/GB2016/050297, dated Apr. 25, 2016—9 Pages.

(Continued)

*Primary Examiner* — Deborah D Carr
(74) *Attorney, Agent, or Firm* — RatnerPrestia

(57) ABSTRACT

A method of fractionating a mannosylerythritol lipids (MELs) containing composition by loading the composition onto an adsorbing support, separating a fraction which is enriched in MELs from the support using supercritical carbon dioxide, and optionally separating one or more further fractions enriched in MELs from the support using supercritical carbon dioxide and an optional co-solvent. The MELs can be obtained at high concentration by using only "green" solvents.

19 Claims, 10 Drawing Sheets

(51) Int. Cl.
  *C11B 3/10* (2006.01)
  *A23D 9/013* (2006.01)
  *B01D 11/04* (2006.01)
  *B01D 15/08* (2006.01)
  *C12P 7/64* (2006.01)
  *B01D 11/00* (2006.01)

(52) U.S. Cl.
  CPC .......... *B01D 11/0492* (2013.01); *B01D 15/08* (2013.01); *C11B 3/006* (2013.01); *C11B 3/10* (2013.01); *B01D 2011/007* (2013.01); *C12P 7/64* (2013.01)

(58) Field of Classification Search
  USPC ........................................................ 554/205
  See application file for complete search history.

(56) References Cited

FOREIGN PATENT DOCUMENTS

| | | |
|---|---|---|
| EP | 2055314 B1 | 6/2013 |
| EP | 2074985 B1 | 7/2013 |
| EP | 2596089 B1 | 12/2014 |
| EP | 2865746 A1 | 4/2015 |
| JP | 2009201478 A | 9/2009 |
| WO | 2011120776 A1 | 10/2011 |
| WO | 2012010405 A1 | 1/2012 |
| WO | 2013026727 A1 | 2/2013 |
| WO | 2013037643 A1 | 3/2013 |
| WO | 2014185805 A1 | 11/2014 |

OTHER PUBLICATIONS

Hubert et al., "New Perspective for Microbial Glycolipid Fractionation and Purification Processes", C.R. Chimie 15 (2012) pp. 18-28.

Novik et al., "A Novel Procedure for the Isolation of Glycolipids from Bifidobacterium Adolescentis 94 BIM Using Supercritical Carbon Dioxide", Journal of Biotechnology 121 (2006) pp. 555-562.

Rakhuba et al., "Application of Supercritical Carbon Dioxide (scCO2) for the Extraction of Glycolipids from Lactobacillus Plantarum B-01", Journal of Supercritical Fluids 49 (2009) pp. 45-51.

Rau et al., "Downstream Processing of Mannosylerythritol Lipids Produced by Pseudozyma Aphidis", Eur. J. Lipid Sci. Technol. 107 (2005) pp. 373-380.

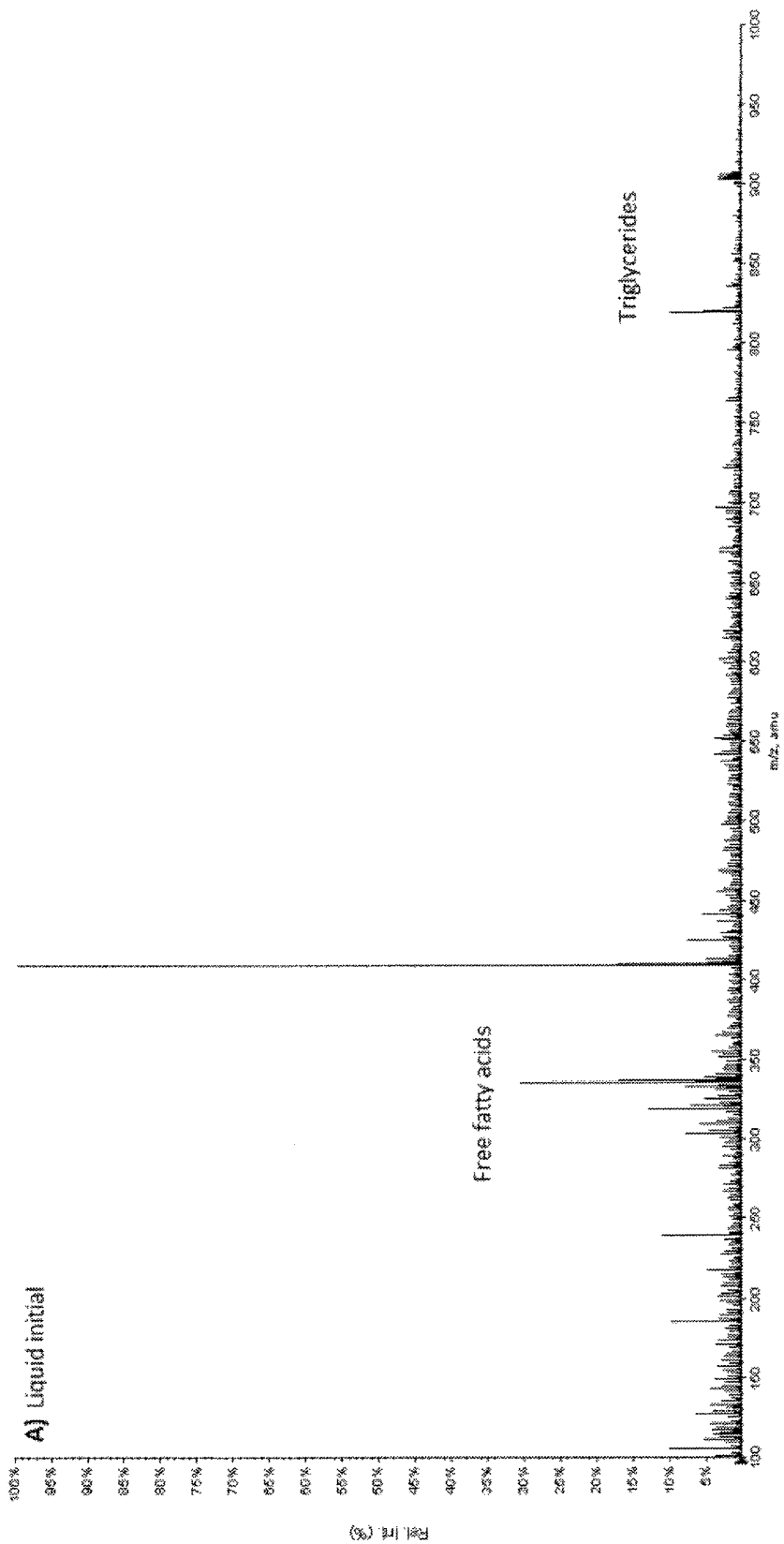

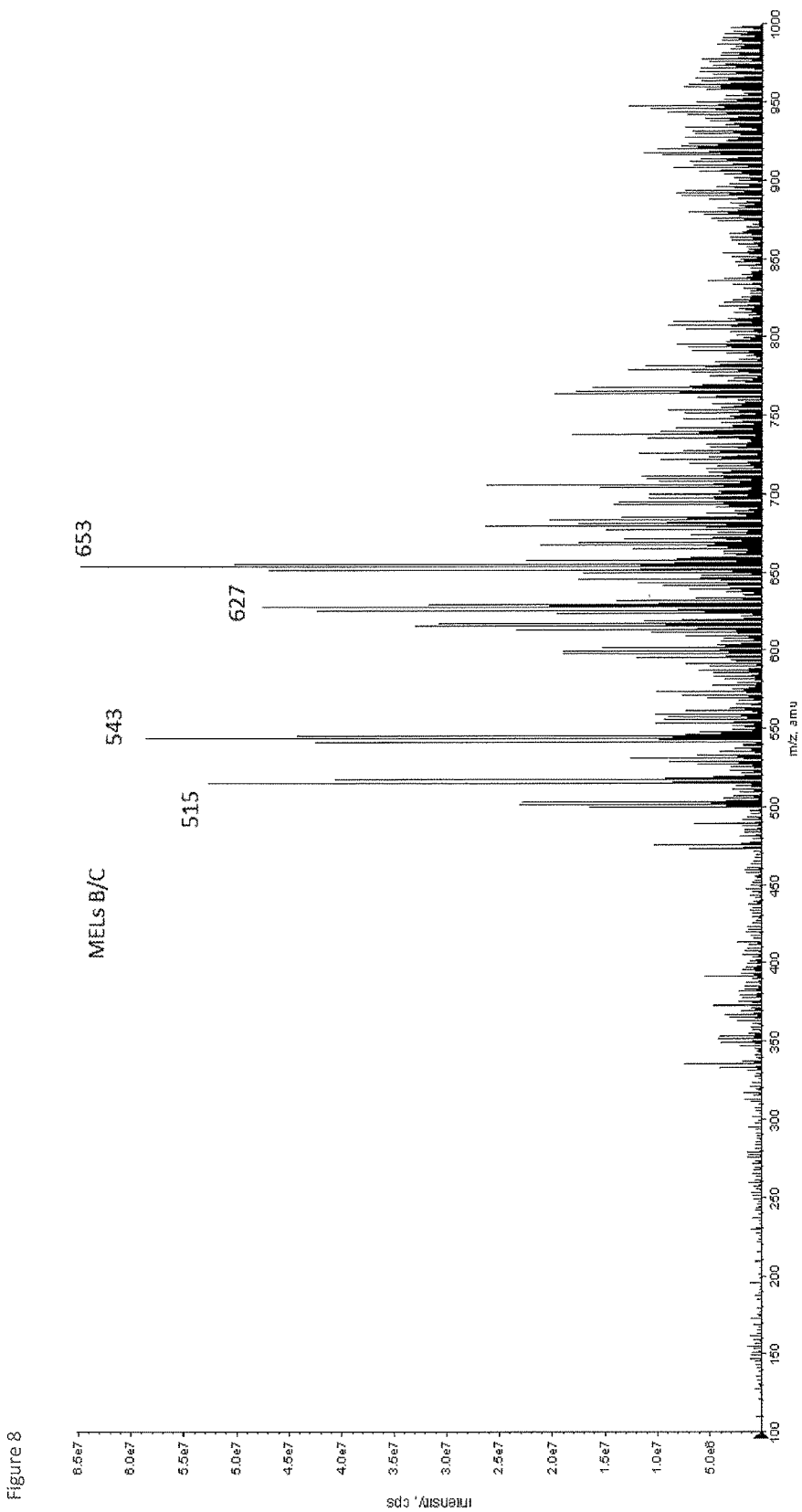

METHOD OF SEPARATING MANNOSYLERYTHRITOL LIPIDS

CROSS REFERENCE TO RELATED APPLICATIONS

This application is the National Stage filing of International Appln. No. PCT/GB2016/050297, filed 9 Feb. 2016, and claims priority of GB Application No. 1505287.1, filed 27 Mar. 2015, the entirety of which applications is incorporated herein by reference for all purposes.

FIELD OF INVENTION

The present invention relates to a method of separating mannosylerythritol lipids (MELs) using supercritical carbon dioxide, in particular when using with a co-solvent.

BACKGROUND

MELs are a group of naturally occurring glycolipids that contain mannose and erythritol as the hydrophilic end, and fatty acids with different carbon chain lengths and degrees of unsaturation in their lipophilic end. They are classified under four groups as MEL-A, MEL-B, MEL-C and MEL-D depending on the acetylation of their hydroxyl groups. The properties of MELs are derived from their amphiphilic character, having potential use as biosurfactants, antimicrobial agents or vehicles for gene and drug delivery.

MELs can be produced by fermentation of a suitable microorganism, for example, *Pseudozyma* sp. produces MELs as a major component, whilst *Ustilago* sp. produces them as a minor component. Although MELs have been known for many years, they have only recently regained attention, particularly as biosurfactants, due to their environmental compatibility, mild production conditions, and structural diversity.

At present no suitable commercially viable method exists for either the isolation or purification of MELs from a crude fermentation medium, or the concentration or separation thereof into their individual groups (A, B, C and/or D) according to the degree of acetylation. In particular, there is a need for such a method which employs only renewable or "green" solvents and does not use potentially flammable or harmful organic solvents such as heptane or hexane.

SUMMARY OF THE INVENTION

We have surprisingly discovered a method of separating or fractionating MELs which overcomes or significantly reduces at least one of the aforementioned problems.

Accordingly, the present invention provides a method of fractionating a MEL-containing composition which comprises, (i) loading the composition onto an adsorbing support, optionally (ii) separating a fraction from the support using liquid carbon dioxide, (iii) separating a fraction which is enriched in MEL from the support using supercritical carbon dioxide, and optionally (iv) separating one or more further fractions enriched in MEL from the support using supercritical carbon dioxide and an optional co-solvent.

The invention further provides a method of fractionating a MEL-containing fermentation broth which comprises, (i) dewatering the broth, (ii) loading the dewatered composition onto an adsorbing support, (iii) separating a fraction from the support using liquid carbon dioxide, (iv) separating a fraction which is enriched in MEL from the support using supercritical carbon dioxide, and optionally (v) separating one or more further fractions enriched in MEL from the support using supercritical carbon dioxide and an optional co-solvent.

The invention also provides a method of fractionating a MEL-containing composition which comprises, (i) loading the composition onto an adsorbing support, optionally (ii) separating a fraction from the support using liquid carbon dioxide, (iii) separating a fraction which is enriched in MEL from the support using supercritical carbon dioxide, and (iv) separating one or more further fractions enriched in MEL from the support using supercritical carbon dioxide and an optional co-solvent.

The invention yet further provides a composition selected from the group consisting of (a) 85 to 99.9 wt % of MEL A and 0.1 to 15 wt % of glycerides; (b) 85 to 99.9 wt % of MEL B and 0.1 to 15 wt % of glycerides; (c) 85 to 99.9 wt % of MEL C and 0.1 to 15 wt % of glycerides; (d) 85 to 99.9 wt % of the combined amount of MEL B and MEL C and 0.1 to 15 wt % of glycerides; and (e) 85 to 99.9 wt % of MEL D and 0.1 to 15 wt % of glycerides.

The invention still further provides the use of supercritical carbon dioxide to fractionate a MEL-containing composition.

Mannosylerythritol lipids (MELs) can be produced by cultivation of a MEL-producing microorganism. The general Formula (1) shows the chemical structure of conventional MELs. The chemical structure includes 4-O-β-D-mannopyranosyl-meso-erythritol as the basic unit thereof.

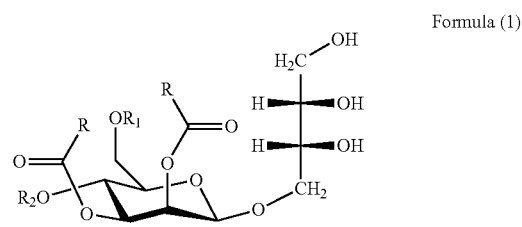

Formula (1)

Four kinds of MELs are known according to whether an acetyl group at 4- and 6-positions of mannose is present or not. The four kinds are designated MEL-A, MEL-B, MEL-C, and MEL-D.

In MEL-A, both of $R_1$ and $R_2$ are acetyl groups. In MEL-B, $R_1$ is an acetyl group and $R_2$ is hydrogen. In MEL-C, $R_1$ is hydrogen and $R_2$ is an acetyl group. In MEL-D, both of $R_1$ and $R_2$ are hydrogen.

Each substituent R in FIG. 1, which may be the same or different, is a hydrocarbon group, suitably an alkyl group or alkenyl group, preferably a C4-C24, more preferably C6-C18, and particularly a C6-C14 alkyl or alkenyl group.

The number of carbon atoms in the substituent R of the MEL-A, MEL-B, MEL-C, and/or MEL-D varies according to the number of carbon atoms in the fatty acid constituting triglyceride in the fats and oils included in a MEL-producing medium and the degree of assimilation of fatty acids by the MEL producing microorganism. In the case where the triglyceride includes an unsaturated fatty acid residue, it is possible for MEL to include the unsaturated fatty acid residue as the substituent R.

Each resulting MEL is generally a mixture of compounds having different fatty acid residues of the substituents R.

Other isomers, e.g. optical isomers, of the MELs shown in FIG. 1 exist and the method of the present invention is equally applicable to these.

The adsorbing support used in the present invention is preferably a solid particulate material. The support can be neutral, basic or acidic and can be selected from any suitable support material known in the art. The support is preferably inert towards both the MELs and any of the other components present in MEL-containing composition. By "inert" is meant that adsorption occurs by physical means and there is no significant or substantial chemical interaction with the support.

The support preferably has a large surface area and may be selected from any, preferably inert, small particle size and/or porous material. The support is typically selected from the group consisting of sand, glass beads, silica, alumina, montmorillonite, magnesium silicate, aluminium silicate, zeolite, polystyrene beads, chitosan, and polysaccharide. In one preferred embodiment, the support is sand which is preferably dried, e.g. in a kiln before use.

Suitable support material can for example be selected from Celite S, Celite 110, Celite 209, Celite 281, Celite 503, Celite 512M, Celite 545, Celite 545AW, Celite 560, Celite 577F, Celite 535a (all ex Celite Corp.); acid Alumina (Alumina A), basic Alumina (Alumina B), neutral Alumina (Alumina N), Ascarite and Florisil (ex Sigma-Aldrich), Bentonite, Kaolinite, Fuller's Earth (ex Sigma-Aldrich), silica gel 60A 40-63 µm (ex Fluorochem LC301SP).

The support material may have one or more of the following properties;
  pores having a diameter in the range from 3 to 50 nm, more preferably 7.5 to 30, and particularly 10 to 20 nm;
  porosity in the range from 0.5 to 6 $cm^3/g$, more preferably 1 to 4 $cm^3/g$, and particularly 1.5 to 3 $cm^3/g$;
  specific surface area in the range from 2 to 400 $m^2/g$, more preferably 5 to 250 $m^2/g$, and particularly 20 to 150 $m^2/g$; and/or
  average particle diameter in the range from 0.5 to 200 µm, more preferably 1 to 150 µm, and particularly 5 to 100 µm.

The nature of the support has an influence on the binding strength between the support and the adsorbed material. Materials such as Celite or bentonite may have little binding strength. Alternatively the support may be an acidic, neutral or basic alumina and offer strong binding. The support is selected or tailored according to the desired level of separation, and/or according to the nature of the material to be separated. It is observed for example, that moving from neutral to acidic alumina support results in a shift in fraction distribution towards more polar fractions and greater support interaction.

In one embodiment, the MEL-containing composition is or is derived from a MEL-containing fermentation broth. MEL-containing fermentation broths are preferably obtained by growing a suitable micro-organism, preferably a strain of *Pseudozyma* (e.g. *P. aphidis, P. Antarctica*, or *P. graminicola*) in a medium containing a nutrient source such as yeast extract; a nitrogen source such as ammonium salt, nitrate, or urea; an energy source such as glucose and feeding with a supplement of fatty acids (as triglyceride or free fatty acid).

The composition of the MEL-containing fermentation broths may vary greatly. The main constituents that need to be removed are free fatty acids, and glycerides including mono-, di- and triglycerides.

The concentration of MELs in the MEL-containing fermentation broth is preferably in the range from 0.01 to 25 wt %, more preferably 0.1 to 10 wt %, particularly 0.5 to 5 wt %, and especially 1.0 to 2.5 wt %, based on the weight of the broth.

The MEL-containing fermentation broth is preferably dewatered by any of the methods known in the art. For example the fermentation broth may be dewatered by one or more of heating, centrifuging, decanting, freeze-drying or distilling. In a preferred embodiment centrifugation, particularly liquid:liquid centrifugation is used.

The amount of water removed in the dewatering step is preferably in the range from 30 to 99.9%, more preferably 50 to 99%, particularly 75 to 98%, and especially 85 to 95% by weight based on the original weight of MEL-containing fermentation broth.

In one embodiment, the MEL-containing composition which is loaded onto the support according to the present invention is a dewatered fermentation broth. The concentration of MELs in the MEL-containing composition, preferably dewatered fermentation broth, which is loaded onto the support is preferably in the range from 1 to 70 wt %, more preferably 5 to 50 wt %, particularly 10 to 40 wt %, and especially 15 to 35 wt %, based on the weight of the composition.

The MEL-containing composition is suitably loaded onto the support by mixing with the support, with stirring in a beaker at room temperature, e.g. for 10 to 20 minutes until a homogeneous mixture is achieved. The amount MEL-containing composition in the loaded support is preferably in the range from 1 to 70 wt %, more preferably 2 to 30 wt %, particularly 5 to 25 wt %, and especially 10 to 20 wt %, based on the total weight of the mixture.

The optional liquid carbon dioxide separation step is preferably performed under at least one of the following conditions; (i) at a temperature in the range from 0 to 30° C., more preferably 3 to 20° C.; (ii) at a pressure in the range from 40 to 600 bars, more preferably 60 to 200 bars; (iii) at a flow rate in the range from 1 to 400 kg carbon dioxide/kg support/min, more preferably 5 to 200 kg carbon dioxide/kg support/min; and/or (iv) for time period in the range from 1 to 20 hours, more preferably 2 to 10 hours.

More than one liquid carbon dioxide separation step may be employed, for example with subsequent steps being performed at an increased temperature, pressure and/or flow rate. In one preferred embodiment, no more than one liquid carbon dioxide separation step is employed. The liquid carbon dioxide separation step is preferably used to remove free fatty acids and/or glycerides from the support.

In one embodiment, the MEL-containing composition may be subjected to a fractionation technique prior to adsorption onto the support. For example techniques known in the art such as molecular or short path distillation, vacuum distillation or refrigeration (winterization) may be employed, particularly to remove free fatty acids, prior to adsorption onto the support. In this case, the subsequent liquid carbon dioxide separation step is primarily used to remove glycerides, particularly triglycerides, from the support.

The one or more supercritical carbon dioxide separation steps are preferably performed under at least one of the following conditions; (i) at a temperature in the range from 31 to 80° C., more preferably 35 to 65° C.; (ii) at a pressure of at least 72.8 bars, more preferably in the range from 100 to 600 bars; (iii) at a flow rate in the range from 1 to 400 g carbon dioxide/kg support/min, more preferably 5 to 200 g carbon dioxide/kg support/min; and/or (iv) for time period in the range from 1 to 40 hours, more preferably 2 to 20 hours.

Above the supercritical point of carbon dioxide, the temperature and/or pressure can be selected and adjusted to selectively fractionate MEL-A, MEL-B, MEL C, mixture of MEL B/C, and/or MEL-D.

For any subsequent separations using supercritical carbon dioxide, the temperature and pressure, and/or the use of optional co-solvent, are preferably selected to separate the desired fractions using increasingly polar conditions.

In one preferred embodiment, one or more subsequent separations using supercritical carbon dioxide comprises a co-solvent. The co-solvent is preferably one or more polar, preferably green, solvents, more preferably selected from the group consisting of as water, methanol, ethanol, and mixtures thereof.

The amount of co-solvent used is preferably in the range from 0 to 100 vol %, more preferably 0.1 to 40 vol %, and particularly 1 to 20 vol %, based on the total volume of supercritical carbon dioxide and co-solvent.

In one particularly preferred embodiment, the co-solvent is a mixture of water and ethanol. The ethanol/water mixture employed preferably comprises in the range from 1 to 99.9 vol %, more preferably 10 to 90 vol %, and particularly 60 to 80 vol % of ethanol. The remaining amount of up to 100% preferably comprises, consists essentially of, or consists of water.

In one preferred embodiment, more than one supercritical carbon dioxide separation step using a co-solvent is employed and in each subsequent separation step, the polarity of the co-solvent is increased compared to the previous separation step. The preferred co-solvent is an ethanol/water mixture and the ratio of ethanol:water in the co-solvent is reduced, i.e. the concentration of water is increased, in each subsequent separation step, compared to the previous separation step. In each subsequent separation step, the water content is preferably increased compared to the previous separation step, by an amount in the range from 5 to 30 vol %, more preferably 10 to 25 vol %, and particularly 15 to 20 vol %, based on the total volume of co-solvent.

An advantage of using carbon dioxide as a fractionation and extraction solvent is that it can be easily removed because of its 'zero' surface tension, thereby producing solvent-free products. An advantage of using co-solvents such as ethanol and water is that they can be considered to be 'green' solvents, and the ethanol can be easily removed to produce a composition containing MELs, with substantially no organic solvent present.

The method of the present invention results in an enrichment in the concentration of the MELs. By enrichment is meant an increase in the MELs' concentration compared to the MEL concentration present in the original MEL-containing composition applied to the support. The enrichment can apply to the total amount of MEL A, MEL B, MEL C and MEL D in the composition, and/or to the individual amounts of MEL A, MEL B, MEL C, mixture of MEL B/C, and/or MEL D in the composition.

The MELs concentration is suitably enriched by an amount greater than 400%, preferably in the range from 500 to 1200%, more preferably 550 to 900%, particularly 600 to 800%, and especially 650 to 700% based on the weight of MELs in the original MEL-containing composition applied to the support.

The method of the present invention can surprisingly result in high purity compositions such that the concentration of MELs is suitably greater than 50 wt %, preferably in the range from 60 to 100 wt %, more preferably 70 to 99 wt %, particularly 75 to 97 wt %, and especially 80 to 95 wt % based on the total weight of the composition. The remaining amount of up to 100% preferably comprises, consists essentially of, or consists of glycerides, particularly triglycerides.

In one embodiment, the fractionated composition produced by the method of the present invention comprises, consists essentially of, or consists of (i) greater than 75 wt %, preferably in the range from 80 to 100 wt %, more preferably 85 to 99.9 wt %, particularly 90 to 99.5 wt %, and especially 95 to 99 wt % of MELs, based on the total weight of the composition; and/or (ii) less than or equal to 25 wt %, preferably in the range from 0 to 20 wt %, more preferably 0.1 to 15 wt %, particularly 0.5 to 10 wt %, and especially 1 to 5 wt % of glycerides, particularly triglycerides, based on the total weight of the composition.

The method of the present invention can surprisingly be used to fractionate MELs into their individual components such that compositions can be produced that comprise;

(i) greater than 60 wt %, preferably in the range from 70 to 100 wt %, more preferably 80 to 99 wt %, particularly 85 to 97 wt %, and especially 90 to 95 wt % of MEL-A, based on the total weight of MELs in the composition;

(ii) greater than 60 wt %, preferably in the range from 70 to 100 wt %, more preferably 80 to 99 wt %, particularly 85 to 97 wt %, and especially 90 to 95 wt % of MEL-B, based on the total weight MELs in the composition;

(iii) greater than 60 wt %, preferably in the range from 70 to 100 wt %, more preferably 80 to 99 wt %, particularly 85 to 97 wt %, and especially 90 to 95 wt % of MEL-C, based on the total weight of MELs in the composition;

(iv) greater than 70 wt %, preferably in the range from 85 to 100 wt %, more preferably 90 to 99.5 wt %, particularly 94 to 99 wt %, and especially 96 to 98 wt % of the combined amount of MEL B and MEL-C, based on the total weight of MELs in the composition; or (v) greater than 70 wt %, preferably in the range from 85 to 100 wt %, more preferably 90 to 99.5 wt %, particularly 94 to 99 wt %, and especially 96 to 98 wt % of the combined amount of MEL D, based on the total weight of MELs in the composition.

In one embodiment, the fractionated composition produced by the method of the present invention comprises, consists essentially of, or consists of;

(i) greater than 75 wt %, preferably in the range from 80 to 100 wt %, more preferably 85 to 99.9 wt %, particularly 90 to 99.5 wt %, and especially 95 to 99 wt % of MEL A, based on the total weight of the composition; and less than or equal to 25 wt %, preferably in the range from 0 to 20 wt %, more preferably 0.1 to 15 wt %, particularly 0.5 to 10 wt %, and especially 1 to 5 wt % of glycerides, particularly triglycerides, based on the total weight of the composition;

(ii) greater than 75 wt %, preferably in the range from 80 to 100 wt %, more preferably 85 to 99.9 wt %, particularly 90 to 99.5 wt %, and especially 95 to 99 wt % of MEL B, based on the total weight of the composition; and less than or equal to 25 wt %, preferably in the range from 0 to 20 wt %, more preferably 0.1 to 15 wt %, particularly 0.5 to 10 wt %, and especially 1 to 5 wt % of glycerides, particularly triglycerides, based on the total weight of the composition;

(iii) greater than 75 wt %, preferably in the range from 80 to 100 wt %, more preferably 85 to 99.9 wt %, particularly 90 to 99.5 wt %, and especially 95 to 99 wt % of MEL C, based on the total weight of the composition; and less than or equal to 25 wt %, preferably in the range from 0 to 20 wt %, more preferably 0.1 to 15 wt %, particularly 0.5 to 10 wt %, and especially 1 to 5 wt % of glycerides, particularly triglycerides, based on the total weight of the composition;

(iv) greater than 75 wt %, preferably in the range from 80 to 100 wt %, more preferably 85 to 99.9 wt %, particularly 90 to 99.5 wt %, and especially 95 to 99 wt % of the combined amount of MEL B and MEL C, based on the total weight of the composition; and less than or equal to 25 wt %, preferably in the range from 0 to 20 wt %, more preferably 0.1 to 15 wt %, particularly 0.5 to 10 wt %, and especially 1 to 5 wt % of glycerides, particularly triglycerides, based on the total weight of the composition; or (v) greater than 75 wt %, preferably in the range from 80 to 100 wt %, more preferably 85 to 99.9 wt %, particularly 90 to 99.5 wt %, and especially 95 to 99 wt % of the combined amount of MEL D, based on the total weight of the composition; and less than or equal to 25 wt %, preferably in the range from 0 to 20 wt %, more preferably 0.1 to 15 wt %, particularly 0.5 to 10 wt %, and especially 1 to 5 wt % of glycerides, particularly triglycerides, based on the total weight of the composition.

The following test method was used;

MELs Concentration

The MELs concentration was measured using High Performance Liquid Chromatography-Mass Spectrometry (HPLC-MS). A 5 mg/ml solution of the test fraction in 4:1 methanol:heptane was prepared. The sample was diluted in methanol to 0.03 mg/ml and 10 µl was injected into the HPLC column (Kinetex 5 µm C18 (150×2.10 mm)). The column temperature was 25° C. The elution gradient had the steps shown in Table 1.

TABLE 1

| Time (min) | Flow Rate (µL/min) | A % ($H_2O$) 0.1% formic) | B % (MeOH 0.1% formic) |
|---|---|---|---|
| 0 | 300 | 40 | 60 |
| 25 | 300 | 20 | 80 |
| 45 | 300 | 20 | 80 |
| 75 | 300 | 1 | 99 |
| 105 | 300 | 1 | 99 |
| 106 | 300 | 40 | 60 |
| 115 | 300 | 40 | 60 |

The source used in the MS was an ElectroSpray Ionization in positive mode at a range of 100-1000 m/z. An appropriate calibration curve was produced using standard(s) for the different MELs. The proportion of the different MEL species in the test samples can be compared to their corresponding species in the standard(s) to obtain quantitative values.

The invention is illustrated by the following non-limiting examples.

BRIEF DESCRIPTION OF THE FIGURES

FIG. 8 shows the MS of a supercritical carbon dioxide/ co-solvent fraction from Example 7.

EXAMPLE 1

Figure 1:
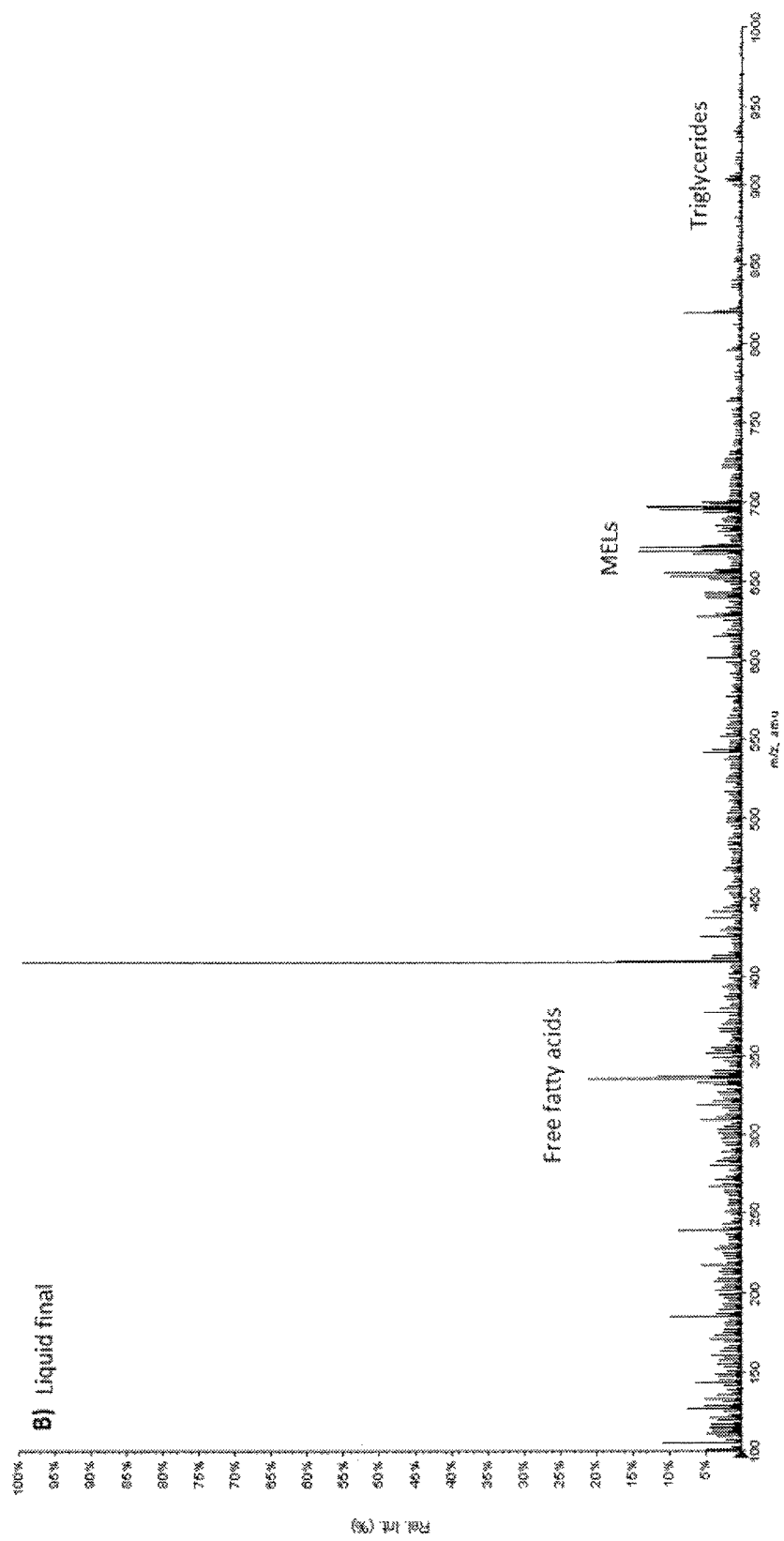
FIG. 1 shows the mass spectrum (MS) of the initial fraction and final fraction of the liquid carbon dioxide step from Example 3. The experiment was carried out with glass beads as support.

MELs were produced at a 25 liter scale using *Pseudozyma aphidis*. 1 ml (1× cryovial) of *Pseudozyma aphidis* (strain DSM 70725) was inoculated into 500 ml of media in a 2 liter shake flask. 2 flasks were grown in a shaker incubator at 120 rpm, and a temperature of 30° C. for 48 hours.

The composition of the inoculum media used is shown in Table 2. The inoculum media was autoclaved at 121° C. for 30 minutes.

TABLE 2

| Nutrients | Concentration (g/L) |
|---|---|
| Glucose | 30.0 |
| Ammonium nitrate ($NH_4NO_3$) | 1.0 |
| Potassium phosphate dibasic ($K_2HPO_4$) | 0.3 |
| Yeast extract (Kerry HY-412) | 1.0 |
| Deionised water | 967.7 |

The 2 culture flasks were added to the production media in a fermenter. The composition of the production media used is shown in Table 3.

TABLE 3

| Nutrients | Concentration (g/kg) | Required (g/25 L) |
|---|---|---|
| Crodafat (rape seed oil fatty acids, ex Croda) | 80.0 | 2000 |
| Sodium nitrate ($NaNO_3$) | 2.0 | 50 |
| Potassium phosphate dibasic ($K_2HPO_4$) | 0.2 | 5 |
| Magnesium sulphate heptahydrate ($MgSO_4 \cdot 7H_2O$) | 0.2 | 5 |
| Yeast extract (Kerry HY-412) | 1.0 | 25 |
| Dow Corning 1510 Antifoam | 1.0 | 25 |
| Deionised water | 915.6 | 22900 |

The composition of the feeds used is shown in Table 4.

TABLE 4

| Feed | Feed rate (g/hr) | Length of feed (hours) | Required (g/25 L) |
|---|---|---|---|
| Crodafat (ex Croda) | 16.6 | 96 | 1593.6 |
| Glucose (50% w/w solution) | 16.6 | 120 | 1992 |

The following fermentation conditions were used;
Temp: 27° C.
pH: Uncontrolled
Air flow: 0.8 vessel volume per minute (20 L/min initially for 25 L fermentation)
DO: Cascade control by agitator rpm to maintain DO (dissolved oxygen) >30%
Length: 7 days
Production feed rates:
  Fatty acid: 16.6 g/hr
  Glucose: 16.6 g/hr The resultant culture was heated to 80° C. and held for 30 minutes. The culture was left to settle without mixing for 30 minutes and the lower (aqueous) layer run off. The upper oily MEL-containing layer was transferred to a container and held at 50° C. for 24 hours and any remaining lower layer formed was removed. The approximate composition of the dewatered material was 70 wt % free fatty acids, 19 wt % triglyceride and 10 wt % MELs. The MEL-containing composition was stored at ambient temperature (5-30° C.) until use.

EXAMPLE 2

Extraction experiments were carried out on a Thar SFC-1000 extraction rig.

The support was prepared as follows;

(i) 1.2 kg of support was weighed into a 2 L rotary evaporator flask.

(ii) 300 g of MEL-containing composition was added in 60 g portions.

(iii) The flask was rotated between the additions to completely disperse the MEL-containing composition and the flask was rotated slowly until a free flowing powder was obtained.

Extraction was then carried out as follows;

(i) The chillers were set at a temperature of 0° C. for the carbon dioxide pump.

(ii) 1.5 kg of the loaded support (powder) was loaded into a 1 L extractor.

(iii) The powder was packed using a plunger to compact the charge and all powder was removed from the inner rim and threads before closing the extractor.

(iv) The carbon dioxide cylinder (ex BOC) was opened, the inline heater and extractor heater were switched off and the separator heated to 45° C.

A first extraction with liquid carbon dioxide was carried out at 5° C. and 100 bar with a flow rate of 10 kg carbon dioxide/kg raw material per hour. Once pressure had been reached, the separator was adjusted to 10 bar back pressure and samples were collected every hour, until the hourly fraction weight was below 1% of the amount of the MEL-containing composition initially adsorbed onto the support. After completion, the carbon dioxide pump was switched off, the separator back pressure was released and the separator was washed with industrial methylated spirits (IMS) and the washings were discarded. The lid was refitted and tightened after thorough drying.

In the first extraction using supercritical carbon dioxide, the automated back pressure regulator (ABPR) was set to 300 bar and the extractor temperature was increased to 40° C. Once temperature was reached, carbon dioxide was turned on at a flow rate of 10 kg carbon dioxide/kg raw material per hour, and once the pressure had been reached, the separator was adjusted to 10 bar back pressure. The separator fraction was collected each hour until the hourly fraction was below 1% of amount of the MEL-containing composition initially adsorbed onto the support. After completion, the carbon dioxide pump was switched off, the back pressure was released and the separator washed out with IMS. The washings were discarded and the separator was reassembled.

A second extraction using supercritical carbon dioxide was carried out with ethanol-water (7:3 by volume) as co-solvent. The co-solvent pump was primed, and the valve was slowly opened to allow pressure to equilibrate with the supercritical carbon dioxide flow. The carbon dioxide flow was turned on at a flow rate of 9 kg carbon dioxide/kg raw material per hour and once pressure had been reached, the separator was adjusted to 10 bar back pressure and the co-solvent pump was opened at a flow rate of 1 L ethanol-water/kg raw material per hour corresponding to 10 vol %. The separator was drained every 20 minutes for three hours. After 3 hours, the co-solvent pump was turned off but the carbon dioxide pump was run for another hour, and the collected fraction was added to the fraction collected using the co-solvent.

At the end of the operation the plant was thoroughly cleaned. The plant was depressurised and all heaters turned off. The contents of the extractor were emptied into a plastic beaker and the extractor was cleaned with a vacuum cleaner. The trap and separator were cleaned with IMS, and allowed to dry. The plant was then reassembled.

Identification of the fractionated compounds was determined by Gas Chromatography-Mass Spectrometry (GC-MS), Direct Infusion Mass Spectrometry (DI-MS) and High Performance Liquid Chromatography-Mass Spectrometry (HPLC-MS). In GC-MS, the identification was based on calculated Kovats retention index, comparison with library mass spectra (NIST and Adams) and comparison with standard components. The use of a VF-5 (equivalent to DB-5 or HP-5) column allowed more accurate correlation with the extensive Adams database. With DI-MS and HPLC-MS, identification was based by using standards. The HPLC column used was a Kinetex 5 μm C18 (150×2.10 mm).

EXAMPLE 3

The MEL-containing composition produced in Example 1 was used with soda lime 3 mm diameter glass beads (ex Paul Marienfeld GmbH & Co.) as support and the procedures described in Example 2 were carried out.

The separated yields fractions were—liquid carbon dioxide 68.5 wt %, supercritical carbon dioxide 7.2 wt % and supercritical carbon dioxide/co-solvent 12.6 wt %.

(i) Liquid Carbon Dioxide Separation

FIG. 1 shows the mass spectra of the first and the last liquid carbon dioxide fraction. The free fatty acids and triglycerides are the main compounds appearing in these fractions (M/Z≈300 and ≈900 respectively). Some of the less polar MEL A (M/Zs 669, 695) is beginning to appear towards the end of the liquid step.

(ii) Supercritical Carbon Dioxide Separation

Figure 2:
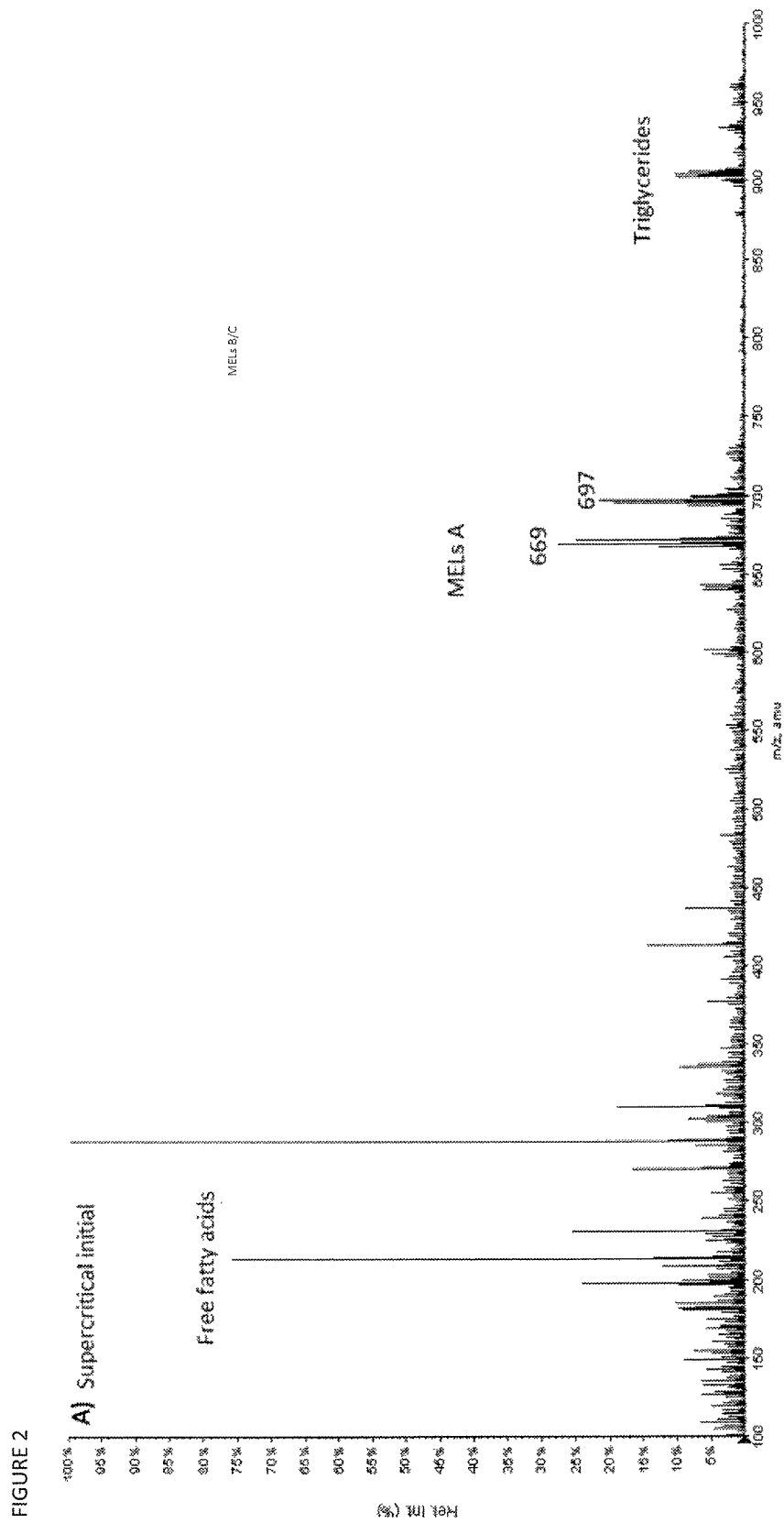
FIG. 2 shows the MS of the initial and final fractions of the supercritical carbon dioxide step from Example 3.
Figure 2:
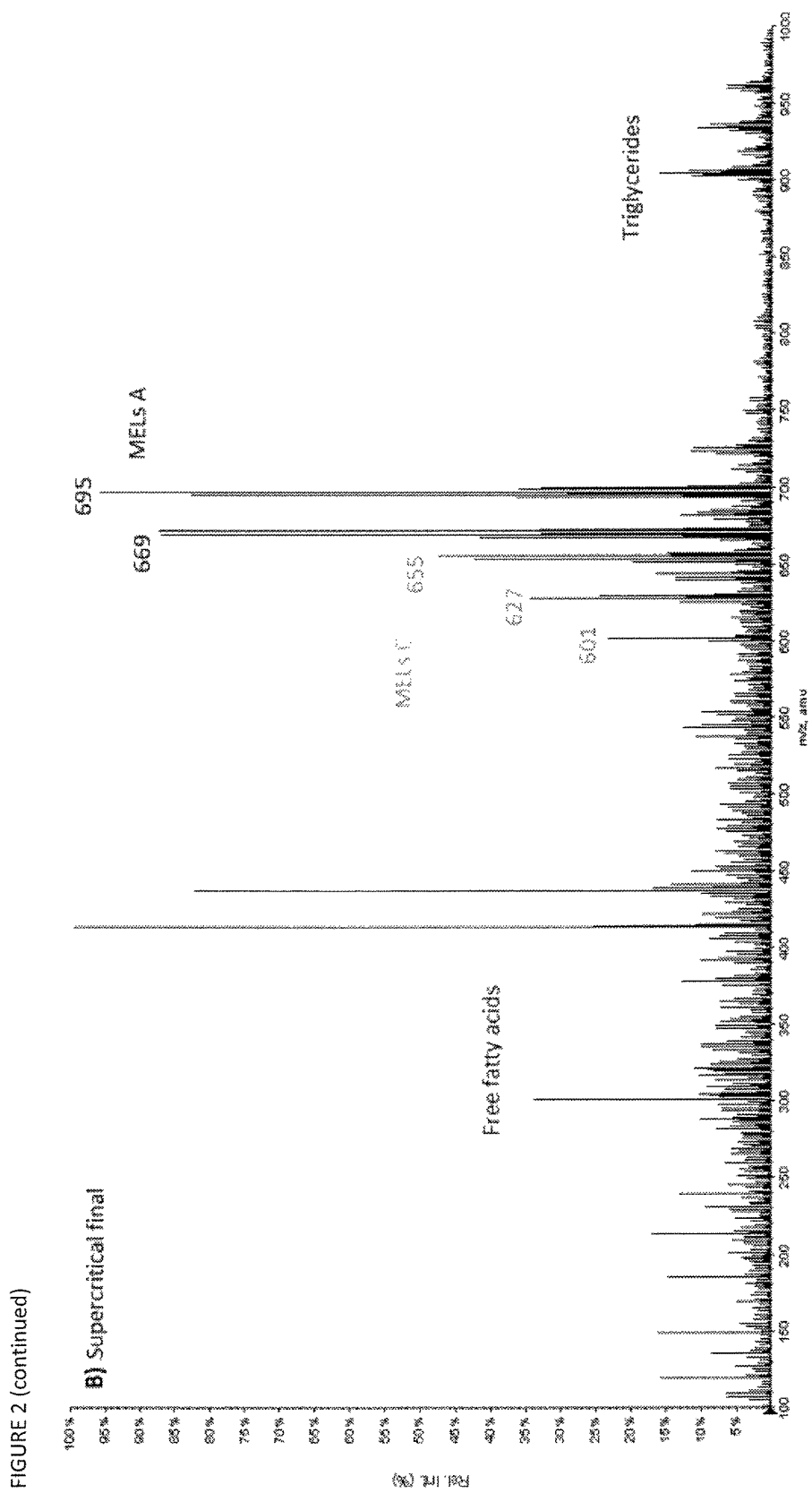

The evolution of the supercritical extraction can be seen in FIG. 2, where in the initial fractions, the proportion of MELs (M/Z≈600-700) is smaller than in the final supercritical fraction. The free fatty acids (M/Z≈200-300) and triglycerides (M/Z≈900) are the other main components in the samples. Some of the MELs appear in the fractions, being enriched towards the end of the supercritical step. The MELs B/C (M/Z 627,655) start to appear in the last fraction of the supercritical step.

(iii) Supercritical Carbon Dioxide/Co-Solvent Separation

Figure 3:
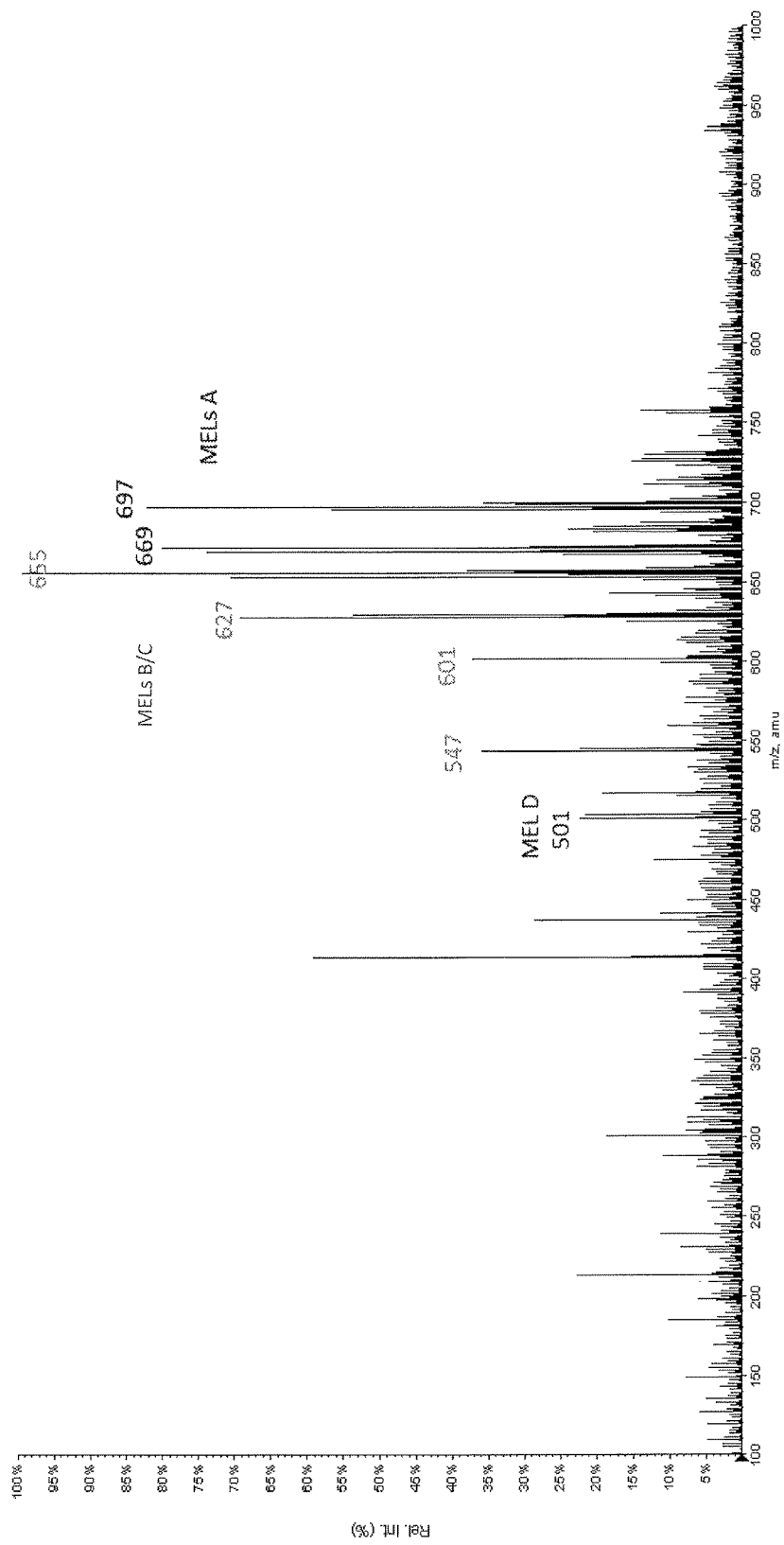
FIG. 3 shows the MS of the supercritical carbon dioxide/ co-solvent fraction from Example 3.

In FIG. 3 it can be seen that the main components in this fraction are the MELs, being present with some triglycerides and free fatty acids as traces. The co-solvent has conferred polarity to the extraction solvent, so more polar compounds can be extracted from the supported matrix. This is the case of the MELs B/C (M/Z 601, 627, 655) and MEL D (M/Z 501) which are being extracted together with the remaining MEL A (M/Z 671, 697, 757).

EXAMPLE 4

The MEL-containing composition produced in Example 1 was used with silica gel (60A 40-63 μm, ex Fluorochem LC301SP) support and the procedures described in Example 2 were carried out.

Figure 4:
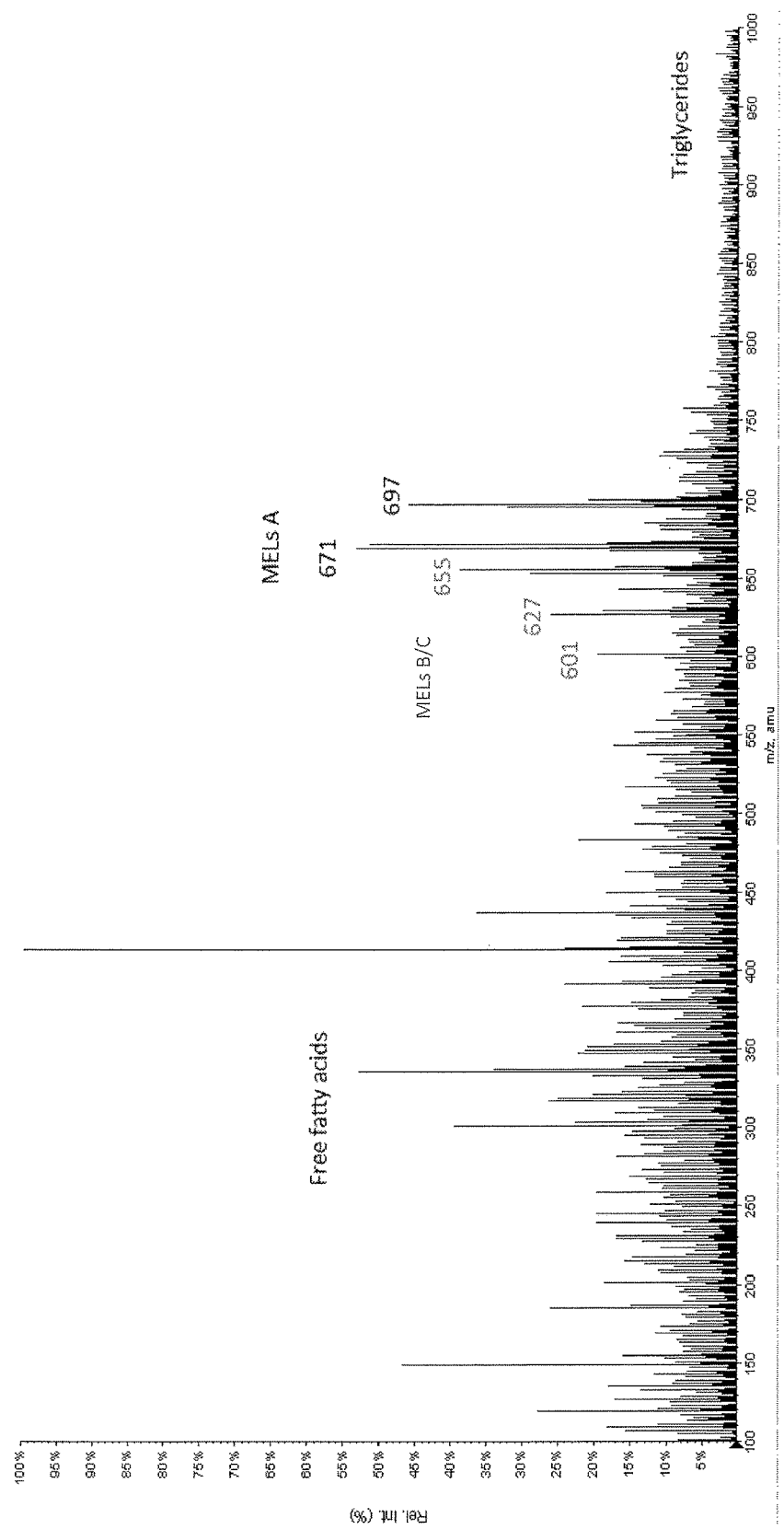
FIG. 4 shows the MS of the supercritical carbon dioxide/ co-solvent fraction from Example 4. The experiment was carried out with silica as support.

The silica support exhibited a higher interaction than the glass beads used in Example 3. The separated yields fractions were—liquid carbon dioxide 28.3 wt %, supercritical carbon dioxide 26.5 wt % and supercritical carbon dioxide/co-solvent 26.9 wt %. The MS spectrum (FIG. 4) of the supercritical carbon dioxide/co-solvent fraction shows free fatty acids (M/Z≈300-400) together with MEL A (M/Z 671, 697) and MEL B/C (M/Z 627, 655).

EXAMPLE 5

The MEL-containing composition produced in Example 1 was used with non-retentive kiln dried red sand (ex Lafarge Aggregates) support and the procedures described in Example 2 were carried out except that the liquid carbon dioxide extraction was at 150 bar/20° C., and the supercritical carbon dioxide extraction at 300 bar/40° C.

Figure 5:
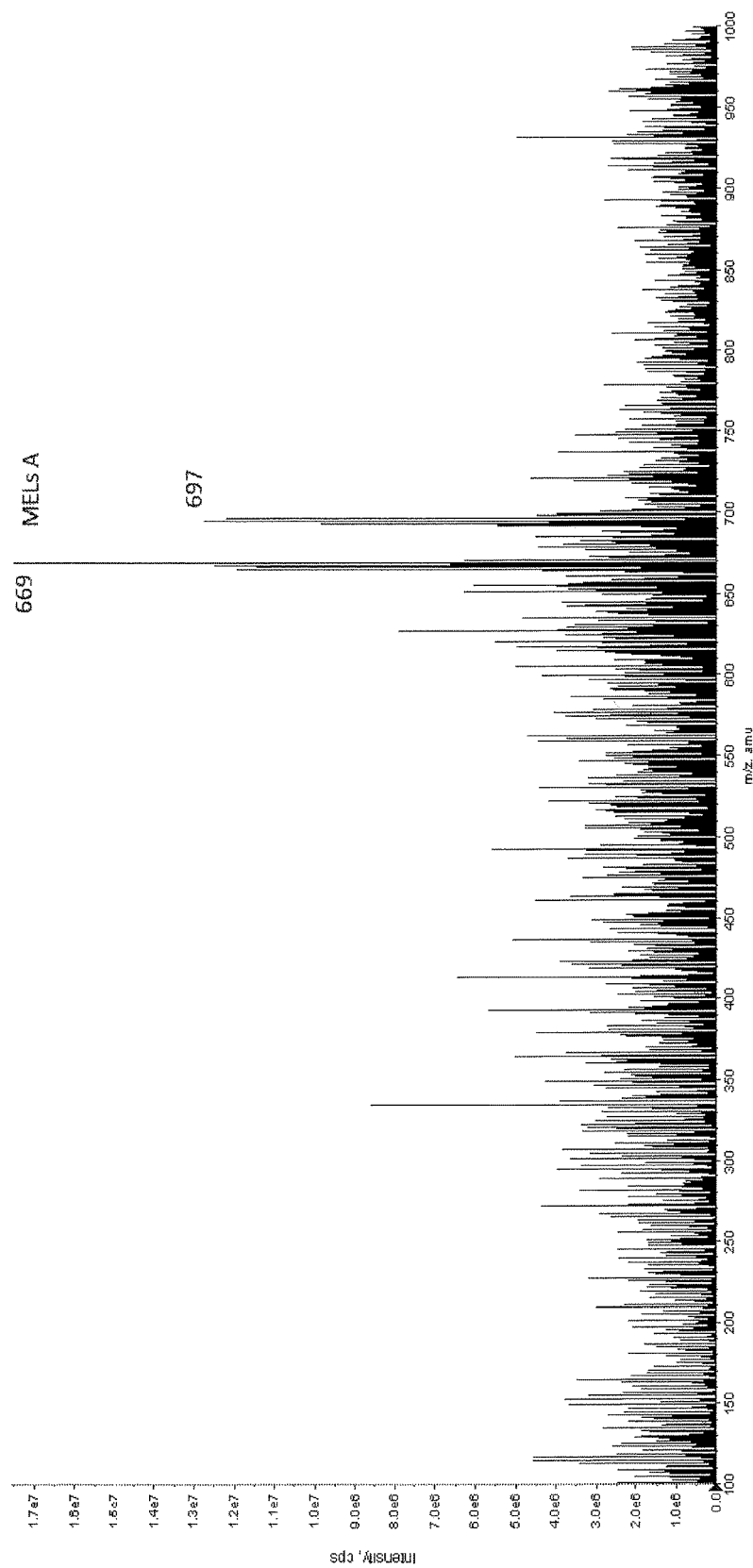
FIG. 5 shows the MS of the supercritical carbon dioxide/ co-solvent fraction from Example 5. The experiment was carried out with kiln dried red sand as support.

The separated yields fractions were—liquid carbon dioxide 69.8 wt %, supercritical carbon dioxide 2.1 wt % and supercritical carbon dioxide/co-solvent 12.8 wt %. The supercritical carbon dioxide fraction MS spectrum (FIG. 5) shows separated MEL A (M/Z 669,697).

EXAMPLE 6

The MEL-containing composition produced in Example 1 was subjected to molecular distillation before conducting carbon dioxide fractionation. Two fractions were obtained by molecular distillation: a light fraction (yielding 70.9 wt % of the starting material) and a heavy fraction (yielding 29.1 wt % of the starting material). The light fraction showed as major components free fatty acids, while no MELs where found. The heavy fraction contained MELs and triglycerides with almost no free fatty acids. The heavy fraction was used with non-retentive kiln dried red sand (ex Lafarge Aggregates) as support and the procedures described in Example 2 were carried out.

Figure 6:
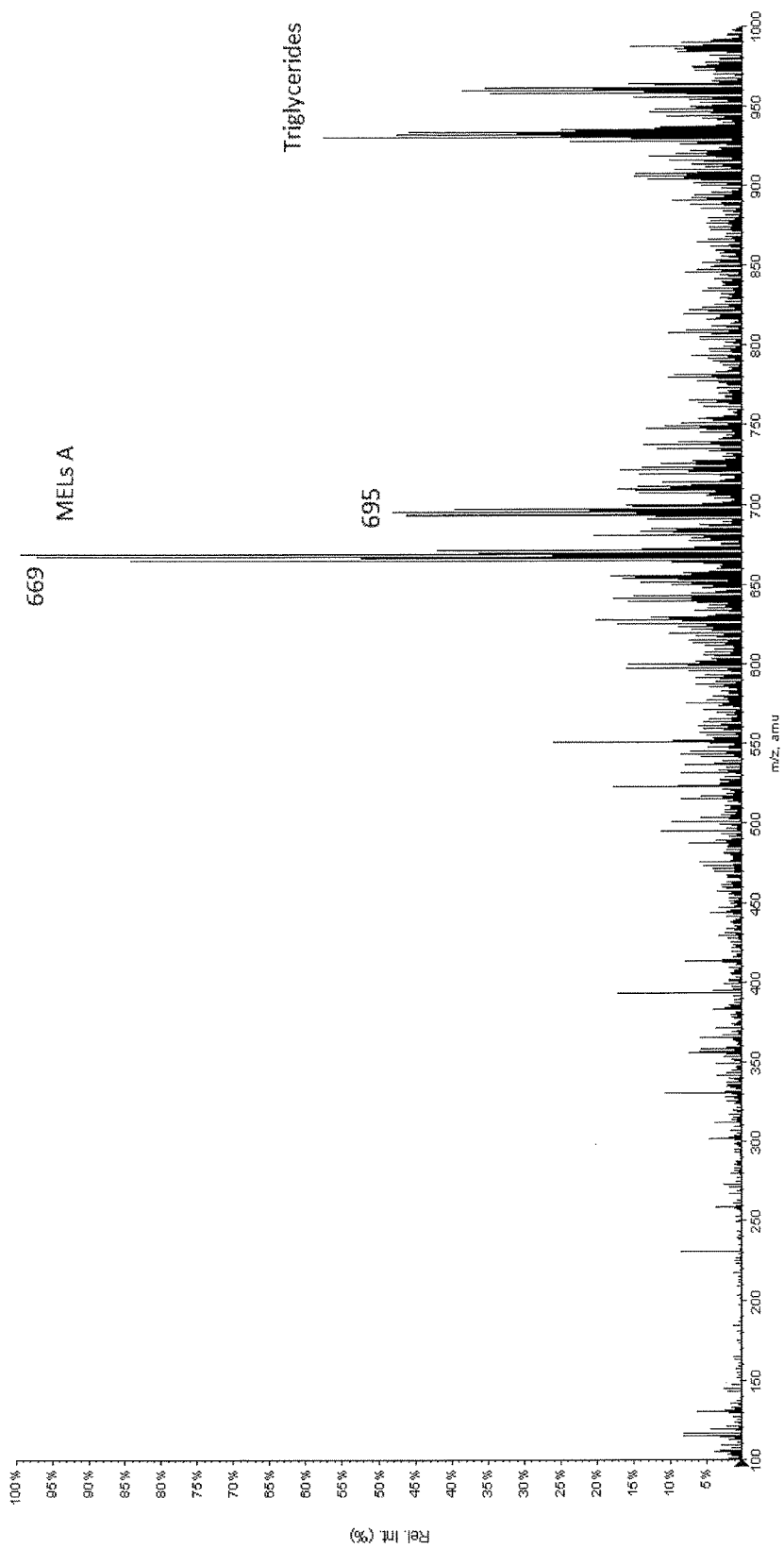
FIG. 6 shows the MS of the supercritical carbon dioxide fraction from Example 6. The experiment was carried out with kiln dried red sand as support.
Figure 7:
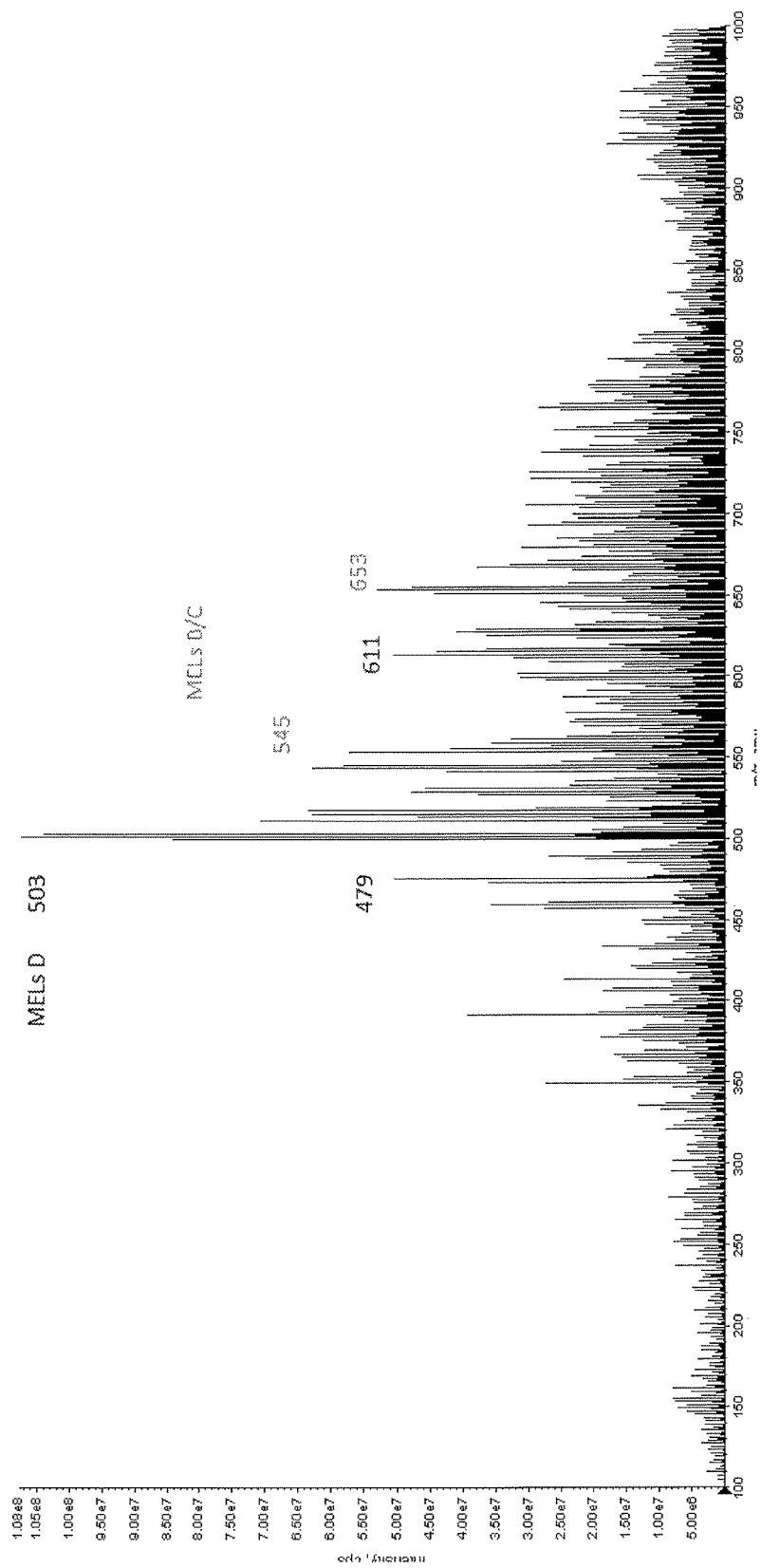
FIG. 7 shows the MS of the supercritical carbon dioxide/ co-solvent fraction from Example 6.

The separated yields fractions were—liquid carbon dioxide 3.4 wt %, supercritical carbon dioxide 47.5 wt % and supercritical carbon dioxide/co-solvent 24.0 wt %. The liquid carbon dioxide and supercritical carbon dioxide fractions contain mainly MEL A (M/Z 667,695) with some triglycerides (see FIG. 6), while the supercritical carbon dioxide/co-solvent fraction contained MEL D and some MELs B/C (see FIG. 7).

EXAMPLE 7

The procedure of Example 6 was repeated except that the co-solvent gradient used (in the procedure in Example 2) was different. The co-solvent fraction was gradually increased in polarity, starting at 2 vol % ethanol, continuing at 4, 8 and 20 vol % ethanol. The final co-solvent fraction was obtained at 10 vol % of an ethanol-water 7:3 mixture. The supercritical carbon dioxide/co-solvent (2 vol % ethanol) fraction contained MELs B/C (see FIG. 8).

The above examples illustrate the improved properties of the method according to the present invention.

The invention claimed is:

1. A method of fractionating a MEL-containing composition which comprises:
   (i) loading the composition onto an adsorbing support,
   (ii) optionally separating a fraction from the support using liquid carbon dioxide,
   (iii) separating a fraction which is enriched in MEL from the support using supercritical carbon dioxide, and
   (iv) optionally separating one or more further fractions enriched in MEL from the support using supercritical carbon dioxide and an optional co-solvent.

2. The method according to claim 1 wherein the MEL-containing composition is a fermentation broth and the method comprises:
   (i) dewatering the broth,
   (ii) loading the dewatered composition onto an adsorbing support,
   (iii) separating a fraction from the support using liquid carbon dioxide,
   (iv) separating a fraction which is enriched in MEL from the support using supercritical carbon dioxide, and
   (v) optionally separating one or more further fractions enriched in MEL from the support using supercritical carbon dioxide and an optional co-solvent.

3. The method according to claim 1 which comprises:
   (i) loading the composition onto an adsorbing support,
   (ii) optionally separating a fraction from the support using liquid carbon dioxide,
   (iii) separating a fraction which is enriched in MEL from the support using supercritical carbon dioxide, and
   (iv) separating one or more further fractions enriched in MEL from the support using supercritical carbon dioxide and an optional co-solvent.

4. The method according to claim 1 wherein the co-solvent is present.

5. The method according to claim 4 wherein the co-solvent is a mixture of ethanol and water.

6. The method according to claim 1 which comprises more than one supercritical carbon dioxide/co-solvent separation steps.

7. The method according to claim 6 wherein the polarity of the co-solvent is increased in a subsequent separation step.

8. The method according to claim 1 wherein the MEL-containing composition comprises 5 to 50 wt % of MELs.

9. The method according to claim 1 wherein at least one of the separated fractions is enriched in MELs by 500 to 1200%.

10. The method according to claim 1 wherein at least one of the separated fractions comprises 70 to 99 wt % MELs.

11. The method according to claim 1 wherein at least one of the separated fractions comprises 80 to 99 wt % of MEL A, or MEL B, or MEL C or MEL D.

12. The method according to claim 1 wherein at least one of the separated fractions comprises 85 to 100 wt % of the combined amount of MEL B and MEL C.

13. A composition selected from the group consisting of:
   (a) 85 to 99.9 wt % of MEL A and 0.1 to 15 wt % of glycerides;
   (b) 85 to 99.9 wt % of MEL B and 0.1 to 15 wt % of glycerides;
   (c) 85 to 99.9 wt % of MEL C and 0.1 to 15 wt % of glycerides;
   (d) 85 to 99.9 wt % of the combined amount of MEL B and MEL C and 0.1 to 15 wt % of glycerides; and
   (e) 85 to 99.9 wt % of MEL D and 0.1 to 15 wt % of glycerides.

14. The composition according to claim 13 wherein the glycerides consist of triglycerides.

15. The composition according to claim 13 which consists of MEL(s) and glyceride.

16. A method of fractionating a MEL-containing composition comprising separating a fraction using supercritical carbon dioxide.

17. The method according to claim 16 further comprising separating a fraction using a supercritical carbon dioxide and a co-solvent.

18. The method according to claim 17, wherein at least one of the separated fractions comprises 70 to 99 wt % of MELs.

19. The method according to claim 17 wherein at least one of the separated fractions consists of 85 to 99.9 wt % of MELs and 0.1 to 15 wt % of glycerides.

* * * * *